US006799471B1

(12) United States Patent
Regimand et al.

(10) Patent No.: US 6,799,471 B1
(45) Date of Patent: Oct. 5, 2004

(54) SYSTEM AND METHOD FOR CONDITIONING AND DETECTION OF MOISTURE DAMAGE IN ASPHALT MIXES

(75) Inventors: Ali Regimand, Raleigh, NC (US); Lawrence H. James, Raleigh, NC (US); Peter D. Muse, Durham, NC (US); Tianging He, Cary, NC (US)

(73) Assignee: InstroTek, Inc., Raleigh, NC (US)

( * ) Notice: Subject to any disclaimer, the term of this patent is extended or adjusted under 35 U.S.C. 154(b) by 0 days.

(21) Appl. No.: 10/460,952

(22) Filed: Jun. 12, 2003

(51) Int. Cl.[7] .............................................. G01N 3/00
(52) U.S. Cl. .......................... 73/803; 73/865.6; 73/73; 137/386; 324/694
(58) Field of Search ............................... 73/803, 865.6, 73/73; 137/386; 324/694

(56) References Cited

U.S. PATENT DOCUMENTS

| | | | | |
|---|---|---|---|---|
| 4,259,868 | A | * 4/1981 | Rao et al. ...................... | 73/597 |
| 4,567,765 | A | * 2/1986 | Rao et al. ...................... | 73/803 |
| 5,365,793 | A | 11/1994 | Terrel et al. ................... | 73/813 |
| 5,969,261 | A | * 10/1999 | McAlister et al. ............. | 73/813 |
| 5,987,961 | A | 11/1999 | Harris et al. ................... | 73/11.01 |
| 6,112,599 | A | * 9/2000 | Maki, Jr. ........................ | 73/801 |
| 6,526,836 | B1 | 3/2003 | Brouse .......................... | 73/818 |

OTHER PUBLICATIONS

ASTM Designation D4867/D 4867M–96—"Standard Test Method for Effect of Moisture on Asphalt Concrete Paving Mixtures".

AASHTO Designation T283–89 "Resistance of Compacted Bituminous Mixture to Moisture Induced Damage".

\* cited by examiner

Primary Examiner—Edward Lefkowitz
Assistant Examiner—Alandra Ellington
(74) Attorney, Agent, or Firm—Michael E. Mauney

(57) ABSTRACT

Apparatus and methods for detection of susceptibility to moisture damage for asphalt mixes. A sample of asphalt mix is placed inside a chamber, which is partially filled with water. An increased air pressure is applied to the chamber. A controlled evacuation of the water from the chamber takes place while the increased pressure is maintained in the chamber. Pressure is released from the chamber and water is returned to the chamber. The cycle is repeated a predetermined number of times. Changes in conductivity and turbidity of the water may be monitored to indicate mixture stripping. When a chosen number of cycles of a pressurized emptying and filling of the chamber is complete, the asphalt sample is removed from the chamber and tested against a controlled sample. The test procedure adapts itself readily to a dual chamber design so that two samples may be tested simultaneously. A vacuum may also be applied to the chamber in addition to pressurizing the chamber. The action of forcing water into a sample and allowing it to bleed out of a sample creates pore pressure and stresses the sample in a way that closely simulates the action of a tire passing over wet pavement. Computerized controls may be used to automate the procedure and to record and display data from sensors.

57 Claims, 3 Drawing Sheets

SYSTEM AND METHOD FOR CONDITIONING AND DETECTION OF MOISTURE DAMAGE IN ASPHALT MIXES

FIELD OF THE INVENTION

This invention relates generally to equipment and method for testing pavement mixes, commonly called asphalt, for the potential for water damage. More specifically, this relates to using water in a pressurized chamber to simulate the action of water being pressed into and pulled out of the wet pavement by tires on asphalt paving on a roadway.

BACKGROUND OF THE INVENTION

Paving mixes known as asphalt consist of approximately 95 percent aggregates and five percent liquid binder. The mixture should be designed to create the best possible bond between the liquid binder and the aggregate. Moisture can penetrate asphalt, which causes an adhesive failure between the binder and the aggregate or water can soften or emulsify the binder film. In either case, water can reduce the strength of the mixture of the asphalt. When the liquid binder is stripped from the asphalt, the aggregate can become scattered or lost. Loss of strength in mixtures can result in pot holes in the pavement or cracking or rutting.

It is well understood that moisture can strip the binder from the aggregates, resulting in a form of failure called "stripping" of an asphalt pavement. The cause of moisture damage to asphalt is multifactorial. First, the type of aggregates used in the mixture affect the susceptibility of the mixture with the binder to moisture damage. For example, residual clay left in aggregates after washing can cause a serious problem. Clay expands when it absorbs the water and creates a barrier between the aggregates and the binder effectively reducing the adhesion or cohesion of the bond between the binder and the aggregates. The composition of the binder also plays an important role in the resistance of the asphalt to moisture damage. The binder viscosity is affected by the mixing temperature in the plant and the ingredients of the binder, such as polymers and rubbers, can also affect the ability of the binder to coat the aggregate surface and to keep the aggregates bound. The binder emulsification has to be controlled to give strength and resistance to moisture for the asphalt. The aggregates should be dried carefully at the plant. Typically, there should be no more than 0.5% moisture retained in the plant produced mix. If water remains in the aggregates, then, during the actual laying of the pavement, steam can be produced which causes stripping of the binder from the aggregate. Controlling the amount of field compaction is necessary to reduce the amount of external water that can penetrate the pavement. A compact pavement with the optimum density and lack of air voids will reduce water permeability, hence reduce the possibility of water damage. However, compaction can be carried too far, which can cause rutting due to mixture instability. If, during construction, there are layers of asphalt mixtures, water can be trapped between the pavement layers. Segregation which is caused by aggregates gradation change when laying down the pavement can have a detrimental affect on asphalt pavement and induce moisture damage. Proper drainage is critical in design and construction of asphalt pavement.

It is apparent, from the above discussion, that susceptibility to water damage or stripping to an asphalt pavement can arise from many sources. Even an ideal mixture of binder and aggregate properly processed or installed can still be susceptible to water damage. Evaluation of moisture susceptibility has become an important part of volumetric design procedure and pavement construction quality control. However, the most important test to determine the susceptibility of water damage for an asphalt mixture requires testing the compacted asphalt mixture in a way that will predict susceptibility of that compacted mixture to water damage.

The most widely used test for moisture sensitivity is covered under American Association of State Highway and Transportation Official (AASHTO) specification T283 and American Society of Testing and Materials (ASTM) D4867. In both of these methods 2 sets of samples of asphalt of approximately 6 inch in diameter by 4 inch thickness are compacted in laboratory compaction equipment. The mixture can be prepared in the laboratory or can be obtained from a field site. One set is saturated with water and is kept in a temperature controlled water bath at 60° C. for 17 to 24 hours. The control set is kept at room temperature (25° C.). In some situations (cold climates), the sample set is also kept at 0° C. for extended time to provide a climatic cycle of cold to hot. Both conditioned (sample) and unconditioned (control) sets are then placed in a break press and broken to determine the pressure at which the sets break apart. The ratio of unconditioned (control) to conditioned (sample) sets break pressure is then used to determine the sensitivity of the mixture to moisture damage. If this ratio {(Conditioned sample strength/Unconditioned sample strength)*100} is over 70, then the mixture passes this test and is deemed acceptable. A visual inspection of the broken conditioned sample may reveal adhesion loss and provide useful information in the inspection stage. The acceptance ratio varies and can range from 70 to 85 depending on the agency and the mixture type. Unfortunately, the reliability and repeatability of this test is very poor, the test does not simulate the true dynamics of the field conditions and the results cannot be correlated to the actual field performance.

In an attempt to create pore pressure within a compacted sample and to better emulate the actual field conditions, in 1974, Rudy Jimenez of Arizona introduced the Double Punch method. This method included a compacted sample that was held under load by a punch or a plate from top to bottom of the sample. The sample was kept under water and a sinusoidal load (5–30 psi) was applied to the sample repeatedly. Even though this method could introduce pore pressure within the sample, it still did not simulate the actual dynamics of the water movement in and out of the pavement through tire activity. Furthermore, the testing time is too long and does not correlate to field performance.

Recently, wheel rutting devices have been used to predict stripping and moisture damage. These devices use a small wheel that travels back and forth on a compacted sample that is immersed in 50 C water. Force is applied to the wheel in various amounts. Although these devices can predict the rutting rate in the pavement, the results have not been correlated to stripping or moisture damage.

Another system that has been used in research is called an Environmental Conditioning Chamber (ECS). This device was developed at Oregon State University in 1987. In this test, a sample is placed in a chamber filled with 60 C water and confining pressure of 2.5 in Hg. A conditioning direct load of 200 lbs. is applied on the sample for 0.1 sec. and then released for 0.09 sec. In this device the resilient modulus of the sample is measured before and after the loading/conditioning process. Empirical criteria is developed based on performance of known mixes to establish pass/fail limits for moisture damage. Unfortunately, this test takes 6–18 hours and so far has had poor repeatability. Also, the apparatus needed to conduct this test is extremely expensive and large for a typical laboratory application in the construction industry. This apparatus is mainly used for research and is not widely available.

Harris et al., U.S. Pat. No. 5,987,961, discloses an apparatus for testing asphalt. Rollers are driven over a pair of pavement samples placed in trays beneath the wheels. The samples are placed in trays which are in a water bath. It is controlled by a computer which continuously monitors where the pavement sample is by a displacement transducer. Terrell et al., U.S. Pat. No. 5,365,793, discloses an asphalt sample in a sealed container. A pressure differential is created across the asphalt and passes water or air or a mix through the asphalt sample by the differential pressure between the vacuum and the supply of fluid which flows through the specimen. For the Terrell device, a typical test procedure will take more than twelve hours.

Despite this earlier work it would be an advance in the art to provide an instrument that can be used during design and quality control to determine the stripping potential and moisture susceptibility of an asphalt mix. The device should simulate as far as possible the action of a tire passing over asphalt on wet pavement in which water is forced in and then drawn out of the pores in asphalt by pressure differentials created by passing of the tire. The device should be simple to operate. The cycle of testing should be relatively short in time. It should produce repeatable results.

SUMMARY OF THE INVENTION

The current invention consists of at least one sealable chamber. The test will proceed by preparing two identical compacted asphalt samples. One sample will be a test sample and one sample will be a control. The chamber can be configured to different sized samples. The test sample is placed within the chamber. Water is added to the chamber sufficient to completely cover the test sample. Water temperature can be controlled and changed to simulate environmental effects on the test sample. The air in the remaining portion of the chamber is pressurized. There is an outlet for the water in the chamber, which is forced from the chamber by the pressurized air into a reservoir. After a sufficient predetermined amount of water is forced from the pressurized chamber into the reservoir, pressure within the sealed chamber is released and allowed to return to atmospheric pressure. Pressurized water forced into the test sample during the period of increased pressure will bleed from the test sample in order to equalize pressure within the test sample and the surrounding atmosphere inside the now unpressurized chamber. Water from the reservoir will be returned to the test chamber to cover the test sample. Again, pressure will be applied to the test chamber to repeat the cycle. There are cycles of alternately pressurizing and depressurizing the test chamber. A cycle ordinarily takes around one to ten seconds. In this way, water is first forced into the test sample by the pressurization of the sealed chamber and the sealed test chamber is depressurized causing water to bleed from the test sample. As the alternate cycle of pressurizing and depressurizing continues, a certain amount of binder will bleed out of the test sample and into the water changing the color and conductivity of the water. The change in the color of the water, or its turbidity and the changes in its conductivity, can be tested through commercially available sensors. The number of the cycles of pressure will stop based on a predetermined set of criteria. These criteria can include the number of cycles, the passage of a period of time, the degree of turbidity and/or conductivity of the water. As the predetermined testing cycle is complete, the test sample can be removed from the chamber and alternatively it can be tested for damage caused by the testing cycle. This can be done in a variety of ways including testing the breaking pressure required to break the sample using a press that is commercially available for testing asphalt samples. The test sample break pressure could be compared to the control sample break pressure, thus to determine the affect the test cycles had on the test sample. The current system and its various embodiments provides the means for simulating and accelerating moisture induced damage in asphalt mixtures. Additionally, sensor capabilities are included to monitor the system functions and to measure changes in water turbidity and conductivity. The moisture damage is induced within a compacted sample by varying one or more of the following constraints such as pressure, temperature, cycle speed, liquid composition, and liquid level.

DETAILED DESCRIPTION OF THE DRAWINGS

Figure 1:
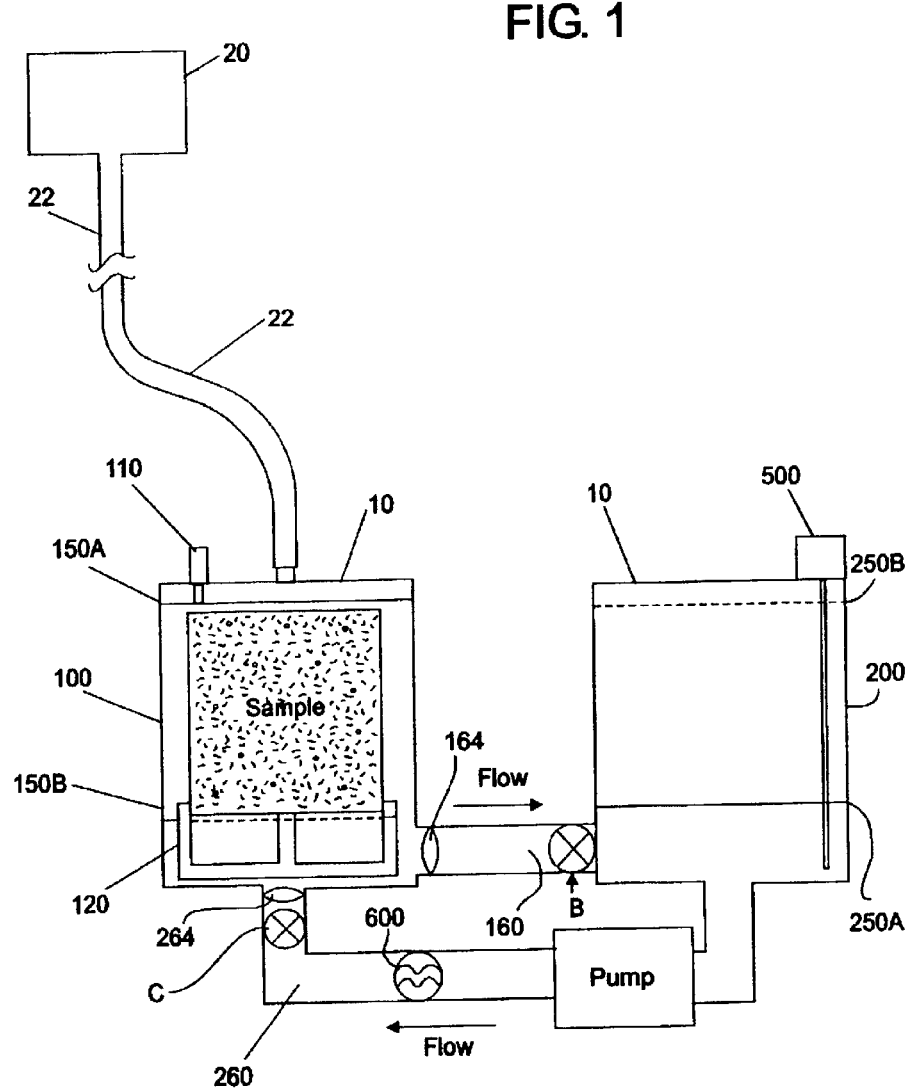
FIG. 1 shows a simplified one test chamber version of the asphalt moisture damage testing device

FIG. 1 shows a simplified one test chamber version of the asphalt moisture damage tester (10). There is a test chamber (100). Placed within the test chamber (100) is an asphalt sample labeled "sample". The sample is placed on the sample support (120). Adjacent to the test chamber (100) is a reservoir chamber (200). The test chamber (100) is connected by an outflow pipe (160) to the reservoir chamber (200). The test chamber (100) is also connected to the reservoir chamber (200) by an inflow pipe (260). The outflow pipe (160) has a restriction valve (B) which allows water to flow in the direction shown by the arrow for outflow pipe (160) from the test chamber (100) to the reservoir chamber (200) while maintaining a specific pressure. Even though water is flowing from the test chamber (100) to the reservoir chamber (200) through the restriction valve (B), a constant elevated pressure may be maintained in the test chamber (100) by continuously pressurizing the air in the test chamber (100). The cross section of the restriction valve (B) will control the amount of fluid or the volume of fluid flowing through the outflow pipe (160) to the reservoir chamber (200). The fluid flowing into the reservoir chamber (200) will displace air from the reservoir (200). The displaced air will be allowed to freely flow from the reservoir chamber (200) thus maintaining a constant atmospheric pressure in the reservoir chamber (200). Likewise, the inflow pipe (260) has a check valve (C) which allows water to flow from the reservoir chamber (200) into the test chamber (100) in the direction shown by the arrow. Both the inflow pipe (260) and the outflow pipe (160) will have screens (264, 164) to protect against debris that may break off from the sample entering the pipes (260, 160). The test chamber (100) may be closed and sealed, as can the reservoir chamber (200). The reservoir chamber (200) has a heater (500) to be used to keep water in the test chamber (100) and the reservoir chamber (200) at a constant temperature. The test chamber (100) will have a water level sensor (110), which will ordinarily be connected to some kind of controller unit. Typically, the controller unit (not shown) will be a microprocessor controlled device which governs the test protocol and the actual functioning of a commercial embodiment of this invention. However, for simplicity's sake, in FIG. 1 instrumentation like a controller device is not shown. A source of pressurized air (20) is connected to the test chamber (100) by an air hose (22).

A test of a sample might proceed as follows. A sample to be tested would be placed in the test chamber (100). The sample would be placed on the sample support (120) in the test chamber (100). Water would be added to both chambers (100) and (200) to levels (150B) and (250A). The restriction valve (B) in the outflow pipe (160) would be closed and a predetermined additional quality of water would be added to test chamber (100) to completely cover the sample to the level (150A). The test chamber (100) would be sealed. The pressurized air source (20) would be activated and pressurized air at a predetermined pressure would be forced into the test chamber (100) by the air hose (22). A predetermined regulated pressure would be established within the test chamber (100) and maintained for a predetermined period of time. The water within the test chamber (100) and within the reservoir chamber (200) would remain at the water level shown as (150A) in the test chamber (100) and (250A) within the reservoir chamber (200). The restriction valve (B) in the outflow pipe (160) would be opened. The pressurized air within the test chamber (100) would force water from the test chamber (100) through the outflow pipe (160) and through the restriction valve (B) into the reservoir chamber (200). Ordinarily, the water would be allowed to flow from the test chamber (100) until the water level is down to water level (150B). This would increase the water level in the reservoir chamber (200) to a level shown in FIG. 1 as (250B). The reservoir chamber (200) is not pressurized and the rate of flow of the water from the test chamber (100) into the reservoir chamber (200) will be determined by the size of the outflow pipe (160) and the restriction valve (B). Once the predetermined outflow water level (150B) is reached, the pressurized air within the test chamber (100) will be released from the test chamber (100) to return the test chamber (100) to atmospheric pressure. Because the water level in the test chamber (100), at that point in time, will ordinarily be at the level shown as (250B), water from the reservoir chamber (200) will seek to equalize the water level by returning to the test chamber (100) through the inflow pipe (260). Water that has been forced into the sample by the pressure in the test chamber (100) will then "bleed" out of the sample. That is, the water forced into the sample by the higher pressure will seek to equalize the pressure by bleeding out of the sample. The sample within the test chamber (100) may remain exposed to atmospheric pressure for a predetermined period of time and the water level in the test chamber (100) remains at the level (150B) during that period of time. However, to continue the test cycle, water will be pumped from the reservoir chamber (200) by the pump labeled "pump" through the inflow pipe (260) through the check valve (C) until water will completely cover the sample again on the test chamber (100) at the level (150A). Then the test cycle will be repeated in which pressurized air is added to the test chamber (100) from the pressurized air source (20) through the air hose (22). The progress of the test may be monitored by a sensor (600). The sensor (600) can utilize a variety of commercially available sensors to detect change in the water passing through the outflow pipe (160) as the test proceeds. Color changes or turbidity in the water is one way of detecting the effect the test is having on the test sample. Another way of detecting changes is using a sensor to detect conductivity changes in the water passing through the outflow pipe (160). Both changes in turbidity and changes in conductivity may be sensed by the sensor (600) on a continuous real time basis as the asphalt moisture damage tester (10) cycles through the alternate fill and emptying the test chamber (100) and the reservoir chamber (200). The sensor (600) could be electrically connected to the controller unit (not shown) for continuous recorded and displayed data from the sensor (600).

As an automobile drives down an asphalt surface on a rainy day, water is caught between the tire surface and the asphalt as the tire rolls along the asphalt surface. Water is also contained within the treads of the tire and irregularities in the surface of the asphalt. As the tire passes over a particular point on the asphalt surface, pressure is exerted by the weight of the automobile on the water on the tire surface, on the asphalt surface, and in the irregularities within the tire and asphalt and the tire tread. This water is pressurized by the weight of the vehicle as it passes. It is believed this pressurized water is forced into the asphalt by the pressure. After the tire has passed, pressurized water within the asphalt will tend to bleed out of the asphalt back into the surrounding water to equalize the water pressure within the asphalt and outside of the asphalt. Also, the surface tension of the water may create a small vacuum or reduced pressure as the tire passes over and away from a particular place on the pavement. Thus, on a rainy day on a busy asphalt street, water will be continuously pushed into and pulled out of the asphalt by the passing of vehicle tires. As and after the tires have passed, water will bleed out of the asphalt to equalize the pressure. The asphalt moisture damage tester (10) simulates the natural action and interaction between a tire, rain water, and asphalt and does so in circumstances that can be rigidly controlled. First, the water temperature can be controlled by the heater (50). The amount of pressure applied can be controlled by use of the regulated pressurized air pressure source (20), the air hose (22), the sealed test chamber (100), the inflow and outflow pipes (160 and 260), and the restriction valve (B). The water can be pressurized around the sample in the test chamber (100) for a controlled period of time. Likewise, the sample can be exposed to regular atmospheric pressure to allow the pressurized water within the sample to bleed out of the sample in the test chamber (100) for a controlled period of time. The cycles have pressurization and depressurization and can happen in quick intervals or slow intervals depending on control of the operator. Composition of the water within the test chamber (100) can be controlled by the operator mimicking such conditions as acid rain. Once a sample has gone through a predetermined number of cycles, the sample may be removed from the test chamber (100) and tested further to determine if the testing has had a impact on the composition or strength of the test sample. The current system and its various embodiments provides the means for simulating and accelerating moisture induced damage in asphalt mixtures. Additionally, sensor capabilities are included to monitor the system functions and to measure changes in water turbidity and conductivity. The moisture damage is induced within a compacted sample by varying one or more of the following constraints such as pressure, temperature, cycle speed, liquid composition, and liquid level.

Figure 2:
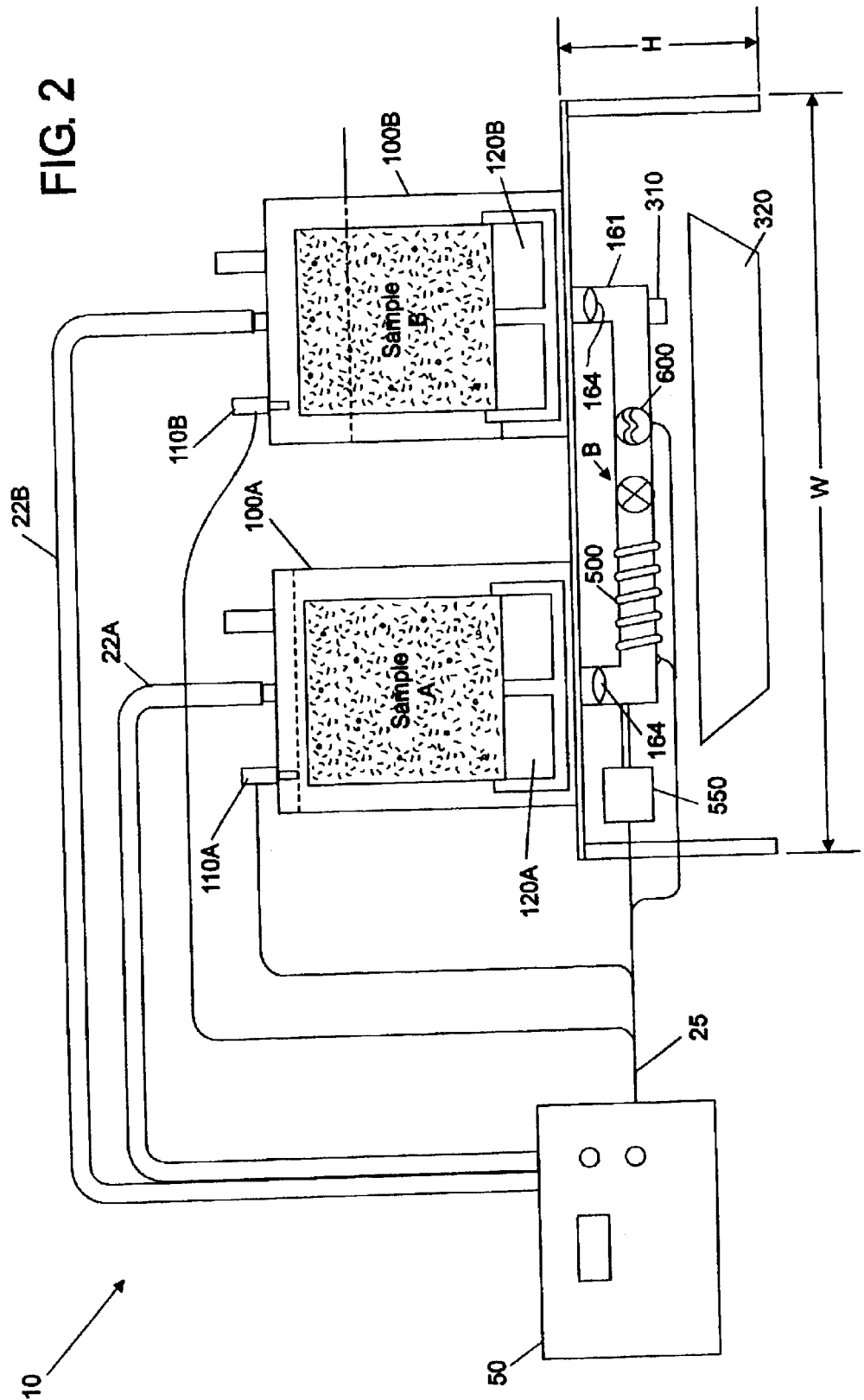
FIG. 2 shows a preferred embodiment of the asphalt moisture damage testing device.

FIG. 2 shows a preferred embodiment of the asphalt moisture damage tester (10). There are two test chambers (100A) and (100B). Additional chambers in multiples of two could easily be added. Each test chamber (100A) and (100B) is loaded with a sample to be tested, respectively sample (A) in test chamber (100A) and the sample (B) in test chamber (100B). Enough water is added to test chambers (100A) and (100B) to fill the connector pipe (161) and to entirely cover the sample (A) in test chamber (100A) and the sample (B) in test chamber (100B). Having multiple chambers allows the user to test similar samples in both chambers or samples with different composition and materials simultaneously. The test chamber (100A) is connected to the test chamber (100B) by a connector pipe (161). Contained within the connector pipe (161) is a sensor (600) and heater element (500) each controlled by the controller unit (50). There are control wires (25) which connect from the controller unit (50) respectively to the sensor (600), the heater (500), water level sensors (110A) and (110B) and water source (550). In the test chamber (100A) the sample (A) is placed on the sample supports (120A). In the test chamber (100B) the sample (B) is place on the sample supports (120B). The test chambers (100A) and (100B) are closed and sealed. The controller unit (50) then can apply air pressure at a specified level to test chambers (100A) and (100B) respectively through air hoses (22A) and (22B). A pressurized air source (not shown) is connected to the controller unit (50). The pressurized air can be generated by many means, such as a hydraulic pump, an electric pump, an air cylinder, membranes with cycling cams, piston, or other technology, which compress air to supply compressed air to the air hoses (22A) and (22B) through the controller unit (50). The application of pressurized air through the air hoses (22A) and (22B) is controlled by the controller unit (50). The controller unit (50) can use electronic means, such as a microprocessor or a central processing unit with appropriate sensors, or manual control valves and a regulator to control the flow of compressed air to the test chambers (100A) and (100B) through the air hoses (22A) and (22B).

To do a test, samples (A) and (B) are placed in each test chamber (100A) and (100B) through a door mechanism (not shown). Water is added to the test chambers (100A) and (100B) to entirely cover both sample (A) and sample (B) in test chambers (100A) and (100B). Door mechanisms are closed and sealed. The door mechanism is designed to be able to completely seal each chamber so that pressure integrity may be maintained throughout the testing process. Compressed air is sent through the air hose (22A) to test chamber(100A) to increase the pressure within that chamber. The first test chamber (100A) pressurizes, which forces water into the sample (A). Test chamber (100B) is not pressurized so water is forced through the connector pipe (161) and the restriction valve (B) so that the water level in test chamber (100B) rises until it reaches a predetermined level. The water level sensor (110B) senses the appropriate water level in test chamber (100B). A signal is sent to the controller (50). At that time, the pressure in chamber (100A) is released and it returns to atmospheric pressure and the pressure in chamber (100B) is increased by compressed air passing through the air hose (22B) to the test chamber (100B). This forces water from the test chamber (100B) through the connector pipe (161) and the restriction valve (B) and also forces it into sample (B). Screens (164) are placed to protect the connector pipe (161) from debris that may break off from sample (A) and/or sample (B). The water level in test chamber (100A) then rises to a point where it is sensed by the water level sensor (110A) in test chamber (100A). It then sends a signal to the controller (50), which then releases the pressure in test chamber (100B) while beginning the pressurization in test chamber (100A) once again, starting the cycle all over again. There is a water source (550) which is controlled by the controller (50). This water source can add water to fill the test chambers (100A) and (100B) as required at the beginning of a test cycle. This water source (550) can also add water during the course of the test itself. The purpose of adding water during the test would be to compensate for evaporation of water and absorption of water by the samples during the course of the test. Loss of any substantial amount of water through evaporation or absorption during a test run could skew the test results and it may be desirable, under some circumstances, to compensate for that lost water. The cycle is repeated with each test chamber (100A) and (100B) being alternately pressurized and depressurized. A sensor (600) senses the changes in conductivity and/or turbidity in the water. It is believed the turbidity and conductivity of the water changes as binder is forced from the asphalt sample by pressure differentials in the water. The turbidity and conductivity can be monitored by a turbidity sensor, such as the APMS 10G Series available through the Honeywell Sensing and Control Company of Freeport, Ill. Some sensor (600) types may be sensitive to pressure and could require a shielded location. When a particular protocol of test cycles have been completed, the samples (A) and (B) can be removed and can be tested with appropriate testing equipment One such testing equipment is a break press, such as the AF850T available through the Prine Instrument Company located in Grove City, Pa. The water in test chambers (100A) and (100B) can be drained through drain (310) into drain basin (320). New samples may be added to begin another test procedure.

Figure 3:
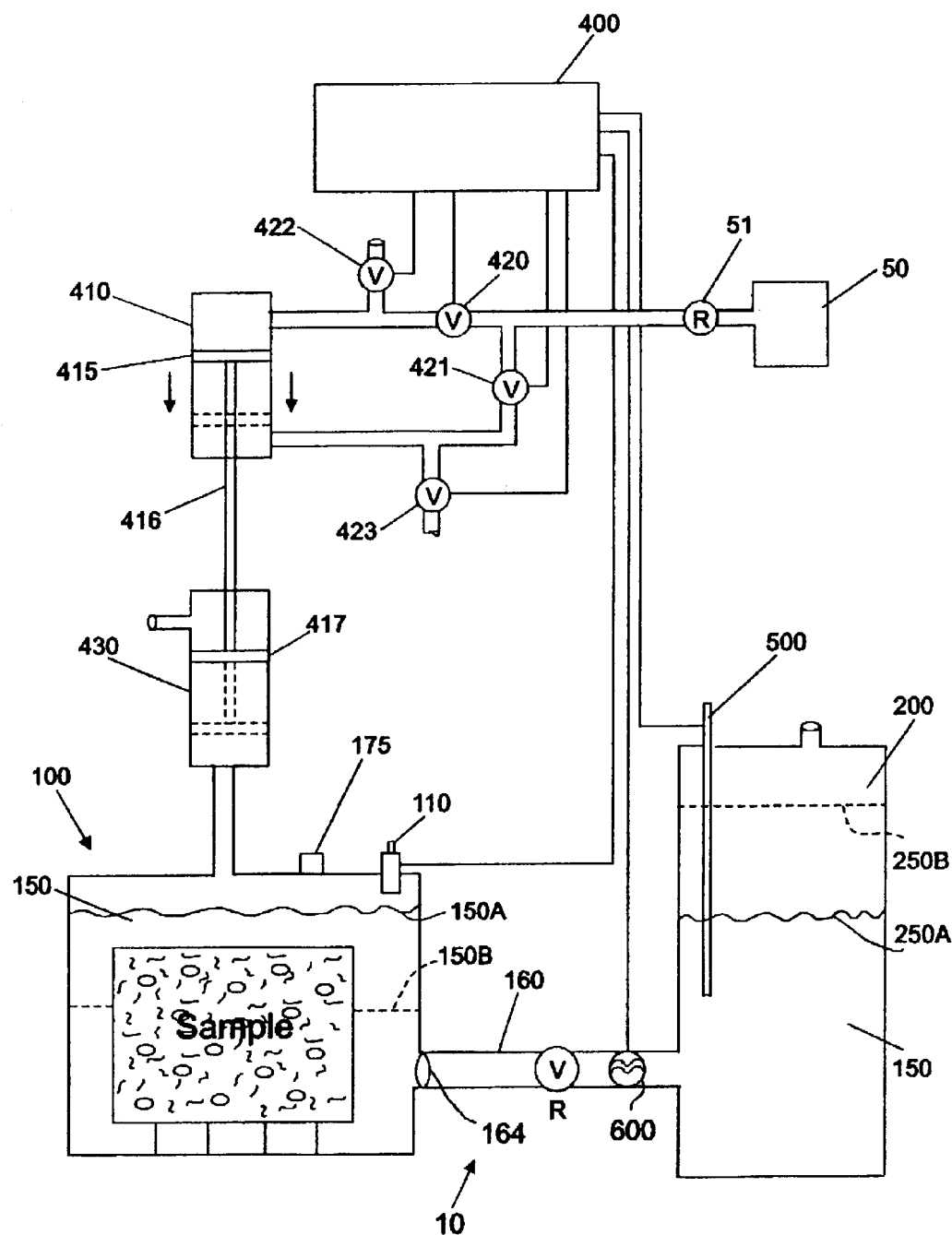
FIG. 3 shows an alternate embodiment of the asphalt moisture testing device that uses vacuum.

FIG. 3 shows an alternate embodiment of the asphalt tester (10) which, in addition to pressure that forces water into a test sample, also employs a vacuum which can pull water from a test sample. There is a controller (400) which is connected to various valves which control the operation of the unit. There is a compressed air source (50) which supplies compressed air through a regulator (51) to operate a master cylinder (410). Contained within the master cylinder (410) is a piston (415) and a drive shaft (416). The controller (400) is connected to valves (420), (421), (422), and (423). To begin operation of the device valve (421) is closed, valve (420) and valve (423) are open and valve (422) is closed. This allows the compressed air source (50) to create an increased pressure in the master cylinder (410) above the piston (415) forcing the piston (415) to move downward in response to the pressure to the portion shown in dotted lines. The slave cylinder (430) has a piston (417) also connected to the shaft (416). As the piston (415) is pushed downward by the pressure created by the compressed air source (50), it pushes down piston (417), which then compresses the air inside the test chamber (100). There is water (150) at a water level (150A) in the test chambers (100) and at water level (250A) the auxiliary chamber (200). The test chamber (100) and the auxiliary chamber (200) are connected by a pipe (160) which has a restriction valve (R) which restricts flow of the water (150) between the test chamber (100) and the auxiliary chamber (200). Consequently, the air in the test chamber (100) as well as the water (150) in the test chamber (100) are compressed as the piston (415) moves down in response to the air pressure applied by the compressed air source (50) through the open valve (420) and the closed valves (421) and (422). As the test proceeds, the water (150) will drop in the test chamber (100) to the point shown as the dotted line as level (150B) in the test chamber (100) and rise to the level (250B) in the auxiliary chamber (200). A screen (164) will be placed in the pipe (160) to protect against debris from the sample. Conductivity and turbidity changes in the water (150) may be monitored by the sensor (600) which is connected to the controller (400).

It is believed that as a tire rolls over a wet pavement, water is not only forced into the pavement by the weight of the tire, but also a small vacuum may be created by the surface tension of the water and the possible adhesion between the tire and the pavement surface which creates a slight vacuum as the tire passes over a part, hence pulling some of the water from the pavement In order to replicate these conditions, the embodiment shown in FIG. 3 can reverse its operation to create a vacuum or reduced pressure inside the test chamber (100). To create a vacuum inside the test chamber (100), the valve (420) and valve (423) will be closed while the valve (421) and valve (422) will be open. The piston (415) will be in the position shown by the dotted lines in the master cylinder (410). Pressurized air will force the piston (415) upward, pulling the shaft (416) upward and necessarily pulling the piston (417) upward as well. The restrictor valve (R) will restrict the flow of water from the position (250B) hence a lowered pressure develops in the test chamber (100). The piston (415) and piston (417) will move up in response to the increased air pressure applied by the compressed air source (50), thus creating a lower than atmospheric pressure inside the test chamber (100). There is a heater (500) in the auxiliary chamber (200) which can heat the water to a constant temperature and maintain the temperature during the course of the test. The heater (500) is connected to the controller (400) by appropriate wires. Water returns to the test chamber (100) until the proper level is sensed by the water sensor (110), which is attached to the controller (500), at which time the process will stop. There is a pressure relief valve (175), which will serve as safety valve in the event pressures are created in the test chamber (100) which could disable the asphalt tester (10) or create a safety hazard. It will be appreciated by one of skill in the art that the foregoing figures and explanations are by way of example and not by way of limitation. The only limitations are the Claims, which follow.

We claim:

1. An apparatus for detection of susceptibility to moisture damage for asphalt mixes comprising:
    (a) at least one chamber, said at least one chamber openable and closeable for receipt of a sample of asphalt mix therein, said at least one chamber sealable when closed;
    (b) means for applying air pressure to said at least one chamber;
    (c) means for filling and emptying said at least one chamber with water;
    (d) means for controlling said means for applying and said means for filling;
whereby a sample of asphalt mix may be placed in said at least one chamber and a cycle of pressurizing said at least one chamber and releasing said pressure combined with filling said at least one chamber with water and emptying said at least one chamber of water simulates the action of water on an asphalt pavement during traffic over that asphalt pavement.

2. An apparatus for detection of susceptibility to moisture damage for asphalt mixes of claim 1 wherein said means for applying further comprises means for controlling said air pressure so that said pressure in said at least one chamber can be controlled to simulate different traffic conditions and different traffic loads.

3. An apparatus for detection of susceptibility to moisture damage for asphalt mixes of claim 2 further comprising means for controlling temperature of said water whereby said temperature may be adjusted to simulate different climatic conditions.

4. An apparatus for detection of susceptibility to moisture damage for asphalt mixes of claim 3 wherein said means for controlling further comprising sensors to sense water level in said at least one chamber whereby said means for filling may be controlled by said means for controlling.

5. An apparatus for detection of susceptibility to moisture damage for asphalt mixes of claim 4 further comprising a means for sensing changes in said water.

6. An apparatus for detection of susceptibility to moisture damage for asphalt mixes of claim 5 wherein said means for controlling receives data from said means for sensing.

7. An apparatus for detection of susceptibility to moisture damage for asphalt mixes of claim 6 further comprising means for screening said means for filling and emptying whereby any debris from said sample of asphalt mix is contained within said at least one chamber.

8. An apparatus for detection of susceptibility to moisture damage for asphalt mixes of claim 7 wherein said means for sensing changes in said water includes means to determine changes in turbidity of said water.

9. An apparatus for detection of susceptibility to moisture damage for asphalt mixes of claim 7 wherein said means for sensing include means to detect changes in conductivity of said water.

10. An apparatus for detection of susceptibility to moisture damage for asphalt mixes comprising:
    (a) a first chamber and second chamber, said chambers connected by a passageway between said first chamber and said second chamber, said first chamber and second chamber open and close for receipt of a sample of asphalt mix, said first chamber and second chamber sealable when closed;
    (b) means for applying air pressure to said first chamber and to said second chamber;
    (c) means for filling and emptying said first chamber and said second chamber with water;
    (d) means for restricting flow of water through said passageway between said first chamber and said second chamber;
    (e) means for controlling said means for applying, said means for restricting, and said means for filling and emptying;
whereby a sample of an asphalt mix may be placed in said first chamber and a sample of asphalt mix placed in said second chamber, pressurizing said first chamber causes water in said first chamber to flow through said passageway to said second chamber, pressurizing said second chamber causes water in second chamber to flow through passageway to said first chamber, thereby simulating the action of water on asphalt pavement during traffic over that asphalt pavement in both said first chamber and said second chamber.

11. An apparatus for detection of susceptibility to moisture damage for asphalt mixes of claim 10 wherein said means for applying further comprising means for adjusting said air pressure so that pressure in said first chamber and pressure in said second chamber can be controlled to simulate different traffic conditions and different traffic loads.

12. An apparatus for detection of susceptibility to moisture damage for asphalt mixes of claim 11 further comprising means for controlling temperature of said water whereby said temperature may be adjusted to simulate different climatic conditions.

13. An apparatus for detection of susceptibility to moisture damage for asphalt mixes of claim 12 wherein said means for controlling further includes water level sensors to sense water level in said first chamber and in said second chamber whereby said means for filling and emptying may be controlled by said means for controlling.

14. An apparatus for detection of susceptibility to moisture damage for asphalt mixes of claim 13 further comprising means for sensing changes in said water.

15. An apparatus for detection of susceptibility to moisture damage for asphalt mixes of claim 14 wherein said means for filling and emptying includes means for screening out debris from said sample of asphalt mix.

16. An apparatus for detection of susceptibility to moisture damage for asphalt mixes of claim 15 wherein said means for controlling receives data from said means for sensing.

17. An apparatus for detection of susceptibility to moisture damage for asphalt mixes of claim 16 wherein said means for sensing changes includes means to determine changes in the turbidity of said water.

18. An apparatus for detection of susceptibility to moisture damage for asphalt mixes of claim 16 wherein said means for sensing includes means to detect changes in conductivity of said water.

19. An apparatus for detection of susceptibility to moisture damage for asphalt mixes of claim 18 wherein said means for controlling further comprises a programmable computerized system that integrates said means for applying, said means for restricting, said means for filling, and said data from means for sensing to carry out a test program and report data from said means for sensing during said test program.

20. An apparatus for detection of susceptibility to moisture damage for asphalt mixes comprising:
(a) at least one chamber, said at least one chamber openable and closeable for receipt of a sample of asphalt mix therein, said at least one chamber sealable when closed;
(b) means for applying air pressure to said at least one chamber;
(c) means for applying vacuum to said at least one chamber;
(d) means for filling and emptying said at least one chamber with water;
(e) means for controlling said means for applying air pressure, said means for applying vacuum, and said means for filling and emptying;
whereby a sample of asphalt mix may be placed in said at least one chamber, pressure may be applied to said at least one chamber followed by a vacuum applied to said at least one chamber combined with filling said at least one chamber with water and emptying said at least one chamber of water to simulate the action of water on asphalt pavement during traffic over that asphalt pavement.

21. An apparatus for detection of susceptibility to moisture damage for asphalt mixes of claim 20 wherein said means for applying air pressure and said means for applying a vacuum are adjustable whereby said apparatus may simulate different traffic conditions and different traffic loads.

22. An apparatus for detection of susceptibility to moisture damage for asphalt mixes of claim 21 further comprising means for controlling temperature in said water whereby said temperature may be adjusted to simulate different climatic conditions.

23. An apparatus for detection of susceptibility to moisture damage for asphalt mixes of claim 22 wherein said means for controlling further includes sensors to sense water level in said at least one chamber whereby said means for filling may be controlled by said means for controlling.

24. An apparatus for detection of susceptibility to moisture damage for asphalt mixes of claim 23 further comprising a means for sensing changes in said water.

25. An apparatus for detection of susceptibility to moisture damage for asphalt mixes of claim 24 wherein said means for controlling receives data from said means for sensing.

26. An apparatus for detection of susceptibility to moisture damage for asphalt mixes of claim 25 wherein said means for filling and emptying further comprises means for screening out debris from said sample of asphalt mix.

27. An apparatus for detection of susceptibility to moisture damage for asphalt mixes of claim 26 wherein said means for sensing changes in said water include means to determine changes in turbidity of said water.

28. An apparatus for detection of susceptibility to moisture damage for asphalt mixes of claim 26 wherein said means for sensing include means to detect changes in conductivity of said water.

29. A method for detection of susceptibility to moisture damage for asphalt mixes comprising:
(a) placing a sample of asphalt mix in at least one test chamber;
(b) adding water to said at least one test chamber containing a sample of asphalt mix therein;
(c) applying an increased air pressure to said at least one chamber;
(d) allowing said water to empty from said at least one chamber while said increased pressure is applied to said chamber;
(e) releasing said increased pressure from said chamber;
(f) returning said water to said chamber to complete at least one cycle of pressurizing the air in said chamber;
(g) testing said water and/or said sample of asphalt mix.

30. A method for detection of susceptibility to moisture damage for asphalt mixes of claim 29 further comprising adjusting said air pressure in said chamber to simulate different traffic conditions and different traffic loads.

31. A method for detection of susceptibility to moisture damage for asphalt mixes of claim 30 further comprising controlling temperature of said water whereby said temperature may be adjusted to simulate different climatic conditions.

32. A method for detection of susceptibility to moisture damage for asphalt mixes of claim 31 further comprising sensing said water level in said at least one chamber to control said water level in said at least one chamber.

33. A method for detection of susceptibility to moisture damage for asphalt mixes of claim 32 further comprising sensing changes in said water in said at least one chamber.

34. A method for detection of susceptibility to moisture damage for asphalt mixes of claim 33 further comprising using a means for controlling to receive data from the sensing of changes in said water in said at least one chamber.

35. A method for detection of susceptibility to moisture damage for asphalt mixes of claim 34 further includes screening said water to remove any debris from said sample of asphalt mix.

36. A method for detection of susceptibility to moisture damage for asphalt mixes of claim 35 further including sensing changes in turbidity of said water.

37. A method for detection of susceptibility to moisture damage for asphalt mixes of claim 35 further including sensing changes in the conductivity of said water.

38. A method for detection of susceptibility to moisture damage for asphalt mixes of claim 29 further comprising providing at least one set of a first and a second test chamber with a passageway for fluid communication between said first and second test chamber in said set.

39. A method for detection of susceptibility to moisture damage for asphalt mixes of claim 38 further comprising placing a first sample of asphalt mix in a first test chamber and placing a second sample of asphalt mix in a second test chamber.

40. A method for detection of susceptibility to moisture damage for asphalt mixes of claim 39 further comprising applying an increased air pressure to one of said first or said second chamber of said set, said increased air pressure emptying the said water from said pressurized chamber to empty through said fluid passageway to the other unpressurized chamber of said set then applying pressure to the previously unpressurized chamber of said set returning thereby said water to the now unpressurized chamber whereby said alternate cycles of applying pressure to said first and second chamber in said set constitutes a cycle of testing.

41. A method for detection of susceptibility to moisture damage for asphalt mixes of claim 40 further comprising adjusting said air pressure in said set to simulate different traffic conditions and traffic loads.

42. A method for detection of susceptibility to moisture damage for asphalt mixes of claim 41 further comprising controlling temperature of said water whereby temperature may be adjusted to simulate different climatic condition.

43. A method for detection of susceptibility to moisture damage for asphalt mixes of claim 42 further comprising sensing water level in each of said first and second chamber in said set to precisely control said water level in said set.

44. A method for detection of susceptibility to moisture damage for asphalt mixes of claim 43 further comprising sensing changes in said water.

45. A method for detection of susceptibility to moisture damage for asphalt mixes of claim 44 further comprising a means for controlling to receive data from said sensing of changes in said water.

46. A method for detection of susceptibility to moisture damage for asphalt mixes of claim 45 further including screening said water to remove any debris from said sample of asphalt mix.

47. A method for detection of susceptibility to moisture damage for asphalt mixes of claim 46 further including sensing changes in turbidity of said water.

48. A method for detection of susceptibility to moisture damage for asphalt mixes of claim 46 further including sensing changes in conductivity of said water.

49. A method for detection of susceptibility to moisture damage for asphalt mixes comprising:
  (a) providing at least one chamber openable and closeable for receipt of a sample of asphalt mix therein, said chamber sealable when closed;
  (b) adding water to said at least one chamber containing a sample of asphalt mix therein;
  (c) applying air pressure to said at least one chamber with said water therein;
  (d) allowing said water to be forced from said at least one chamber by said air pressure;
  (e) applying a vacuum to said at least one chamber;
  (f) allowing said water to refill said at least one chamber from the force of said vacuum;
  (g) testing said water and/or said asphalt sample.

50. A method for detection of susceptibility to moisture damage for asphalt mixes of claim 49 further comprises providing a means for adjusting said air pressure and said vacuum whereby said method for detection may simulate different traffic conditions and different traffic loads.

51. A method for detection of susceptibility to moisture damage for asphalt mixes of claim 50 further comprising providing a means for controlling temperature in said water.

52. A method for detection of susceptibility to moisture damage for asphalt mixes of claim 51 further comprising providing sensors to sense water level in said at least one chamber so that said water level in said at least one chamber may be precisely controlled.

53. A method for detection of susceptibility to moisture damage for asphalt mixes of claim 52 further comprising sensing changes in said water in said at least one chamber.

54. A method for detection of susceptibility to moisture damage for asphalt mixes of claim 53 further comprising using a means for controlling to receive data from the sensing of changes in said water in said at least one chamber.

55. A method for detection of susceptibility to moisture damage for asphalt mixes of claim 54 further comprising screening said water to remove debris from said asphalt mix.

56. A method for detection of susceptibility to moisture damage for asphalt mixes of claim 55 further including sensing changes in turbidity of said water.

57. A method for detection of susceptibility to moisture damage for asphalt mixes of claim 55 further including sensing changes in the conductivity of said water.

* * * * *